(12) United States Patent
Wilson

(10) Patent No.: US 8,851,458 B1
(45) Date of Patent: Oct. 7, 2014

(54) SCENTED AIR VENT ASSEMBLY

(76) Inventor: Fiona Wilson, Deception Bay (AU)

( * ) Notice: Subject to any disclaimer, the term of this patent is extended or adjusted under 35 U.S.C. 154(b) by 294 days.

(21) Appl. No.: 13/540,719

(22) Filed: Jul. 3, 2012

(51) Int. Cl.
*B01F 3/04* (2006.01)

(52) U.S. Cl.
USPC .................................. 261/101; 261/DIG. 88

(58) Field of Classification Search
USPC ........ 261/101, DIG. 88; 96/222; 55/DIG. 35; 239/55, 56, 57
See application file for complete search history.

(56) References Cited

U.S. PATENT DOCUMENTS

| | | | |
|---|---|---|---|
| 4,065,262 A | 12/1977 | Petroff | |
| 4,118,226 A | 10/1978 | Bourassa | |
| 4,563,333 A | 1/1986 | Frigon | |
| 4,604,114 A | 8/1986 | Ward | |
| 5,087,273 A | 2/1992 | Ward | |
| 5,240,487 A | 8/1993 | Kung | |
| D344,327 S | 2/1994 | Tavasso | |
| 5,817,168 A | 10/1998 | Wheless | |
| 2009/0293730 A1 | 12/2009 | Volo et al. | |
| 2010/0254829 A1* | 10/2010 | Harris | ............................ 417/65 |

* cited by examiner

*Primary Examiner* — Robert A Hopkins

(57) ABSTRACT

A scented air vent assembly is provided for attachment to an existing air moving device to scent the air passing through the air moving device. The assembly includes an upper panel having a plurality of upper holes and a lower panel having a plurality of lower holes. The lower panel is coupled to the upper panel and the upper holes are aligned with the lower holes. A medial panel is coupled to and positioned between the upper panel and the lower panel. The medial panel is constructed of a scented material. The medial panel has a plurality of apertures. The medial panel is positioned relative to the upper panel and the lower panel such that the medial panel partially obstructs the aligned upper and lower holes.

16 Claims, 4 Drawing Sheets

SCENTED AIR VENT ASSEMBLY

BACKGROUND OF THE DISCLOSURE

Field of the Disclosure

The disclosure relates to air scenting devices and more particularly pertains to a new air scenting device for attachment to an existing air conditioning unit to scent the air passing through the air conditioning unit.

SUMMARY OF THE DISCLOSURE

An embodiment of the disclosure meets the needs presented above by generally comprising an upper panel having a plurality of upper holes and a lower panel having a plurality of lower holes. The lower panel is coupled to the upper panel and the upper holes are aligned with the lower holes. A medial panel is coupled to and positioned between the upper panel and the lower panel. The medial panel is constructed of a scented material. The medial panel has a plurality of apertures. The medial panel is positioned relative to the upper panel and the lower panel such that the medial panel partially obstructs the aligned upper and lower holes.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
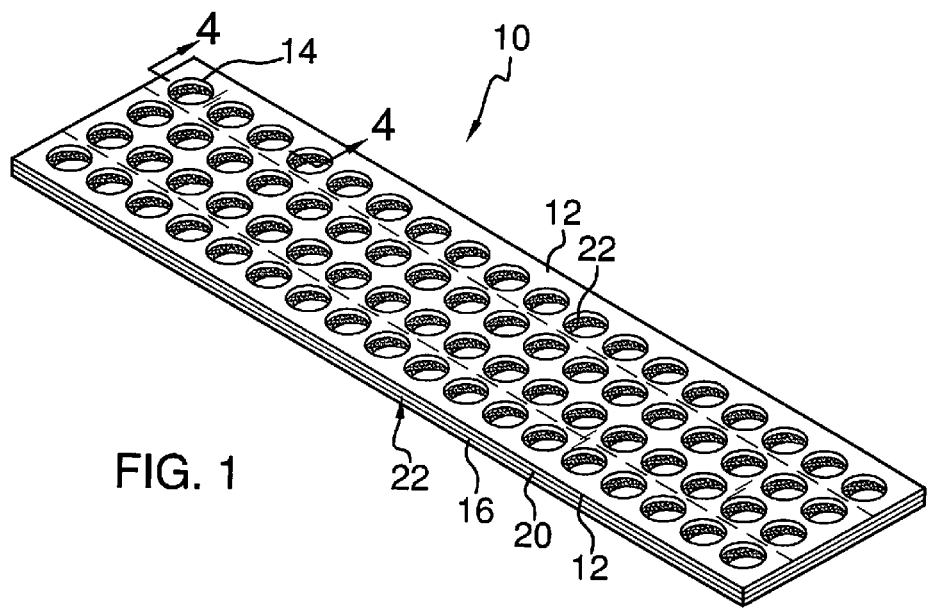
FIG. 1 is a top front side perspective view of a scented air vent assembly according to an embodiment of the disclosure.
Figure 2:
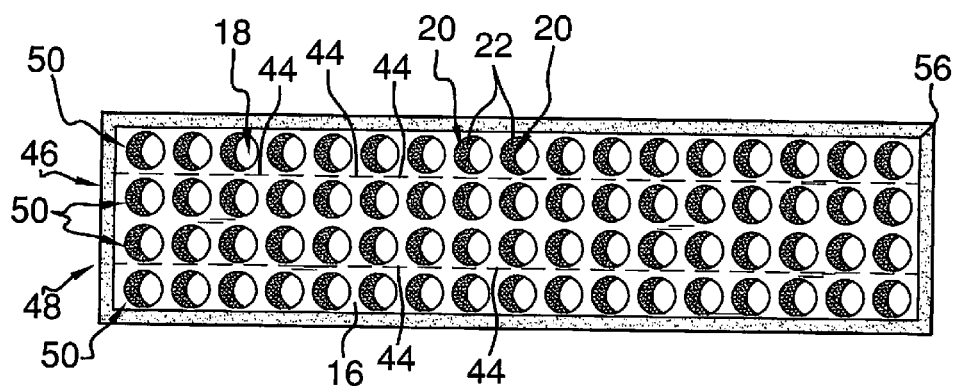
FIG. 2 is a bottom view of an embodiment of the disclosure.
Figure 3:
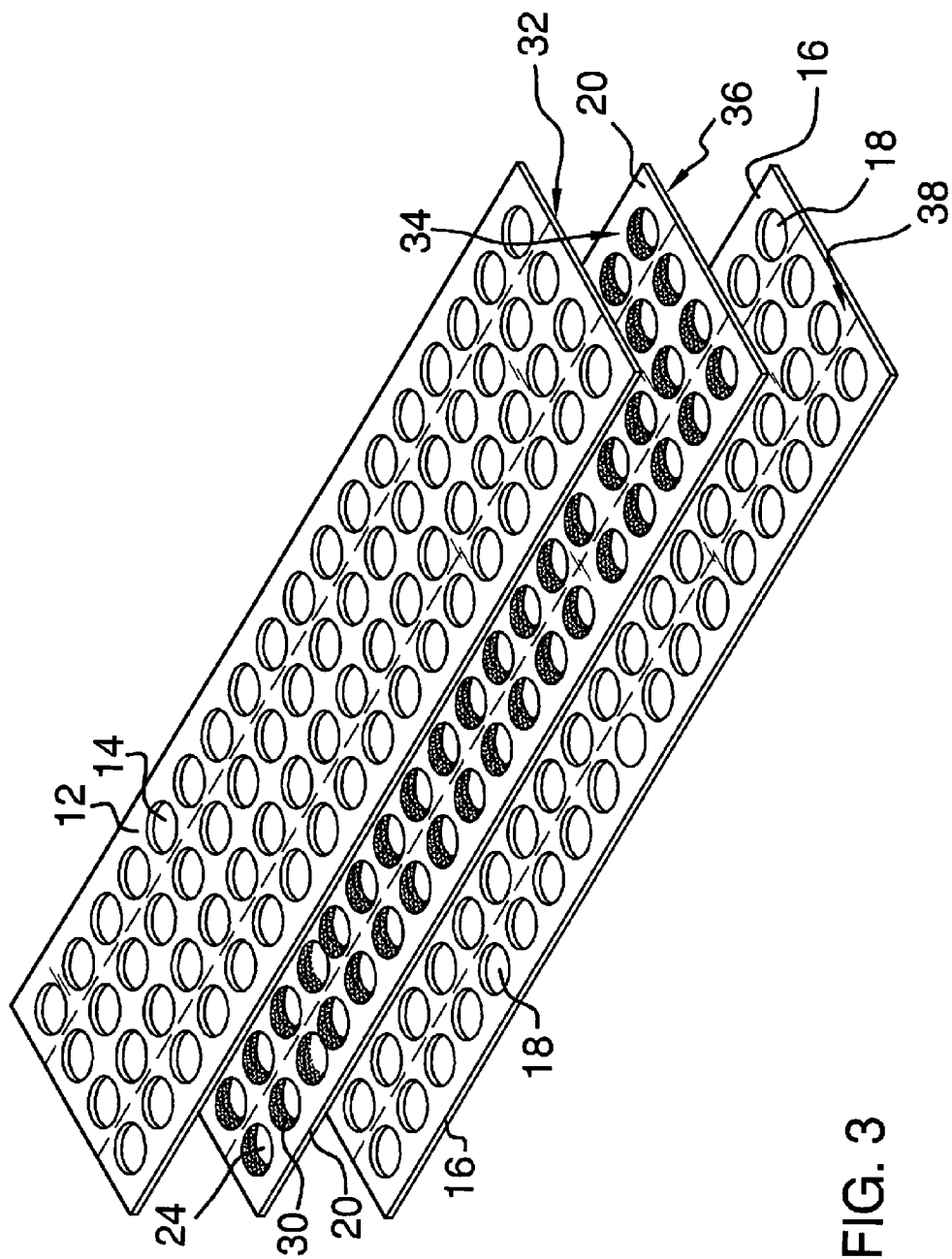
FIG. 3 is an exploded view of an embodiment of the disclosure.
Figure 4:
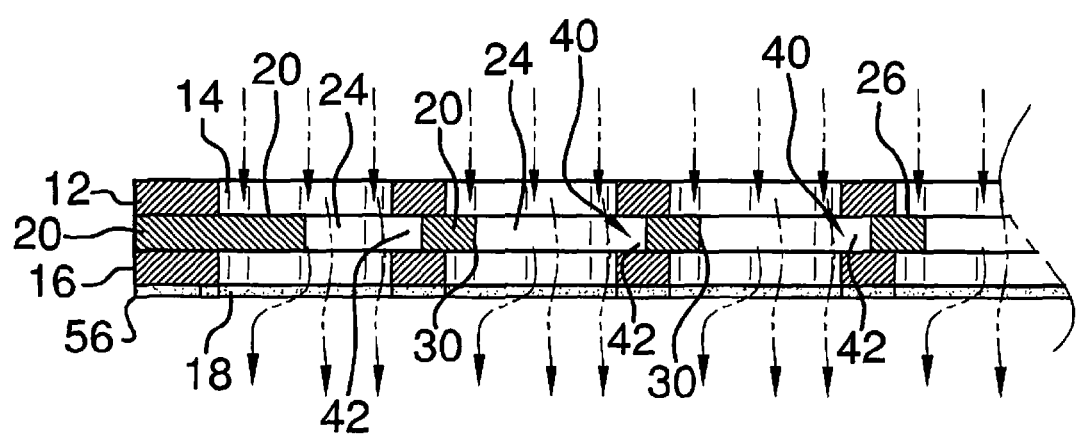
FIG. 4 is a cross-sectional view of an embodiment of the disclosure taken along line 4-4 of FIG. 1.
Figure 5:
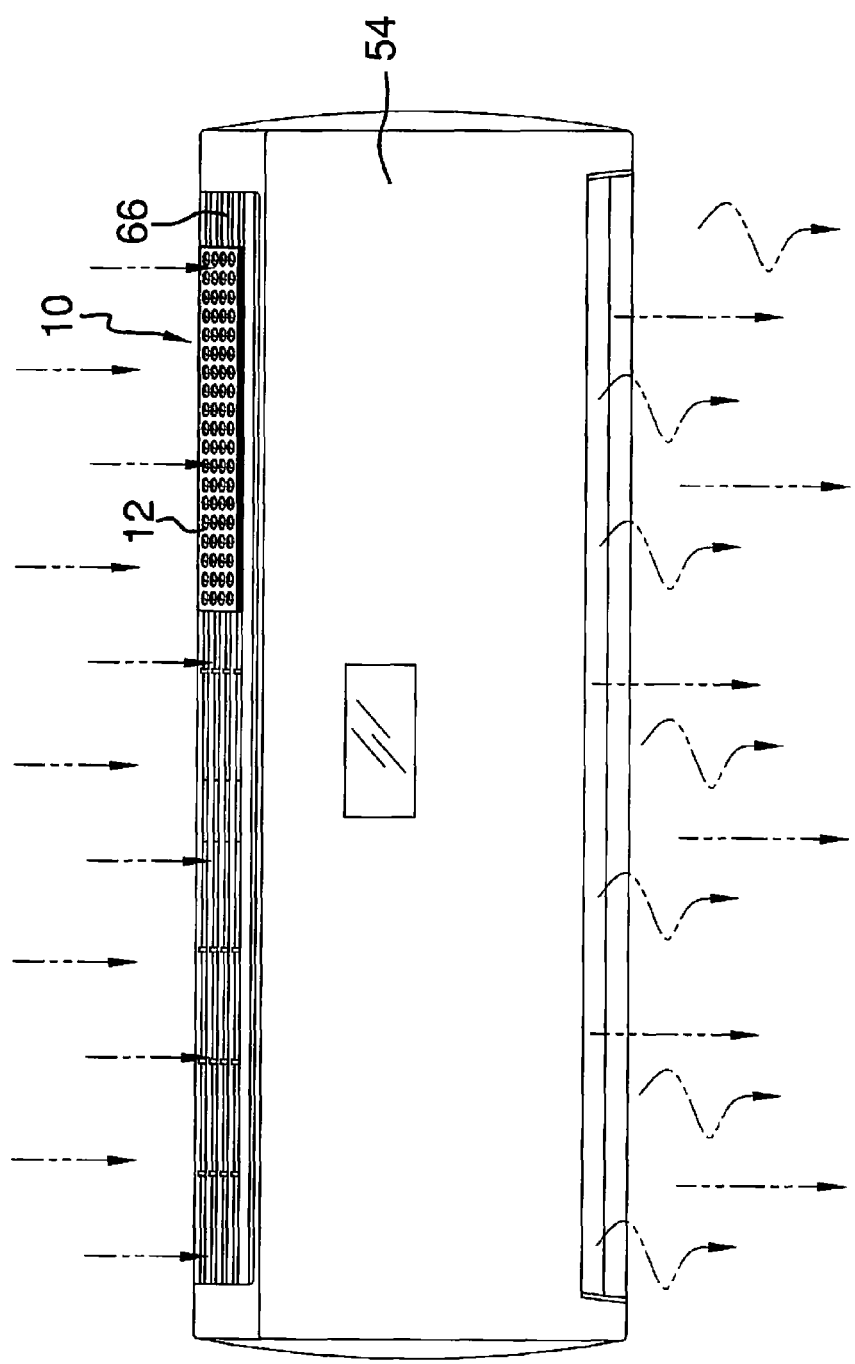
FIG. 5 is a top front perspective view of an embodiment of the disclosure in use.

With reference now to the drawings, and in particular to FIGS. 1 through 5 thereof, a new air scenting device embodying the principles and concepts of an embodiment of the disclosure and generally designated by the reference numeral 10 will be described.

As best illustrated in FIGS. 1 through 5, the scented air vent assembly 10 generally comprises an elongated rectangular shaped upper panel 12 having a plurality of upper holes 14. An elongated rectangular shaped lower panel 16 has a plurality of lower holes 18. The lower panel 16 is coupled to the upper panel 12. The upper holes 14 and the lower holes 18 may be equally sized and aligned vertically. An elongated rectangular shaped medial panel 20 is coupled to and positioned between the upper panel 12 and the lower panel 16. The medial panel 20 is constructed of a scented material 22. The medial panel 20 has a plurality of apertures 24. The apertures 24 may be equally sized with respect to the upper holes 14 and the lower holes 18. The medial panel 20 is positioned relative to the upper panel 12 and the lower panel 16 whereby the medial panel 20 partially obstructs the aligned upper holes 14 and lower holes 18. The medial panel 20 may be constructed of a scent impregnated cardboard material 26 or a scent impregnated gel material 28. Thus, air can flow through the aligned holes 14,18 and pick up scent from a section 30 of the medial panel 20 exposed within the aligned holes 14,18. Conversely, a portion 40 of each aperture 24 is positioned between the upper panel 12 and the lower panel 16 defining a plurality of cavities 42 between the upper panel 12 and the lower panel 16. Each cavity 42 extends from an associated pair of the aligned upper and lower holes 14,18. An adhesive 56 is coupled to an outwardly facing surface 58 of the lower panel 16. Thus, the lower panel 16 is configured for coupling to an air moving device 54 such as a fan or air conditioner unit. The assembly 10 is positionable adjacent to an inlet vent 66 of the device 54 to provide air flow through the aligned holes 14,18.

A lower face 32 of the upper panel 12 abutting an upper face 34 of the medial panel 20. A lower face 36 of the medial panel 20 abutting an upper face 38 of the lower panel 16. A plurality of aligned perforations 44 is positioned in and extend through the upper panel 12, the medial panel 20, and the lower panel 16. The aligned perforations 44 facilitate bending of the upper panel 12, medial panel 20 and lower panel 16 along the perforations 44. The perforations 44 are arranged into a pair of parallel lines 46,48. Each line 46,48 extends between adjacently positioned associated rows 50 of the upper holes 14, the apertures 24, and the lower holes 18. The lines 46,48 of perforations 44 may extend longitudinally across each of the upper panel 12, the medial panel 20, and the lower panel 16 to facilitate bending of the assembly 10 to enhance contact between the adhesive 56 and the air moving device 54.

The upper panel 12 and the lower panel 14 may be constructed of cardboard or another suitable material. The assembly 10 may have a length between 190 and 210 millimeters, a width between 40 and 60 millimeters, and a thickness between 3 and 7 millimeters.

In use, the assembly 10 is coupled to the air moving device 54 to permit air flow through the aligned holes 14,18. The medial panel 20 passively scents that air passing through the assembly 10. After a period of time the assembly 10 may be replaced.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure.

I claim:

1. A scented air vent assembly for coupling adjacent to an inlet vent of an air moving device, said scented air vent assembly comprising:
    an upper panel having a plurality of upper holes;
    a lower panel having a plurality of lower holes, said lower panel being coupled to said upper panel, said upper holes being aligned with said lower holes; and
    a medial panel coupled to and positioned between said upper panel and said lower panel, said medial panel being constructed of a scented material, said medial panel having a plurality of apertures, said medial panel being positioned relative to said upper panel and said lower panel whereby said medial panel partially obstructs said aligned upper and lower holes.

2. The assembly of claim 1, further including said upper holes and said lower holes being equally sized.

3. The assembly of claim 1, further including said medial panel being constructed of a scent impregnated cardboard material.

4. The assembly of claim 1, further including said medial panel being constructed of a scent impregnated gel material.

5. The assembly of claim 1, further including said apertures being equally sized with respect to said upper holes and said lower holes.

6. The assembly of claim 1, further including a lower face of said upper panel abutting an upper face of said medial panel.

7. The assembly of claim 6, further including a lower face of said medial panel abutting an upper face of said lower panel.

8. The assembly of claim 7, further including a portion of each said aperture being positioned between said upper panel and said lower panel defining a plurality of cavities between said upper panel and said lower panel, each said cavity extending from an associated pair of said aligned upper and lower holes.

9. The assembly of claim 1, further including an adhesive coupled to an outwardly facing surface of said lower panel whereby said lower panel is configured for coupling to the air moving device adjacent to the inlet vent.

10. The assembly of claim 9, further including a plurality of aligned perforations in said upper panel, said medial panel, and said lower panel, said aligned perforations facilitating bending of said upper, medial and lower panels along said perforations.

11. The assembly of claim 10, further including said perforations being arranged into a line extending between adjacently positioned rows of said upper holes, said apertures, and said lower holes.

12. The assembly of claim 10, further including said perforations being arranged into a pair of parallel lines, each said line extending between adjacently positioned associated rows of said upper holes, said apertures, and said lower holes.

13. The assembly of claim 12, further comprising:
    each of said upper panel, said medial panel, and said lower panel having an elongated rectangular shape; and
    said lines of perforations extending longitudinally across each of said upper panel, said medial panel, and said lower panel.

14. A scented air vent assembly for coupling adjacent to an inlet vent of an air moving device, said scented air vent assembly comprising:
    an elongated rectangular shaped upper panel having a plurality of upper holes;
    an elongated rectangular shaped lower panel having a plurality of lower holes, said lower panel being coupled to said upper panel, said upper holes and said lower holes being equally sized, said upper holes being aligned with said lower holes; and
    an elongated rectangular shaped medial panel coupled to and positioned between said upper panel and said lower panel, said medial panel being constructed of a scented material, said medial panel having a plurality of apertures, said apertures being equally sized with respect to said upper holes and said lower holes, said medial panel being positioned relative to said upper panel and said lower panel whereby said medial panel partially obstructs said aligned upper and lower holes;
    a lower face of said upper panel abutting an upper face of said medial panel;
    a lower face of said medial panel abutting an upper face of said lower panel;
    a portion of each said aperture being positioned between said upper panel and said lower panel defining a plurality of cavities between said upper panel and said lower panel, each said cavity extending from an associated pair of said aligned upper and lower holes;
    an adhesive coupled to an outwardly facing surface of said lower panel whereby said lower panel is configured for coupling to the air moving device adjacent to the inlet vent; and
    a plurality of aligned perforations in said upper panel, said medial panel, and said lower panel, said aligned perforations facilitating bending of said upper, medial and lower panels along said perforations, said perforations being arranged into a pair of parallel lines, each said line extending between adjacently positioned associated rows of said upper holes, said apertures, and said lower holes, said lines of perforations extending longitudinally across each of said upper panel, said medial panel, and said lower panel.

15. The assembly of claim 14, further including said medial panel being constructed of a scent impregnated cardboard material.

16. The assembly of claim 14, further including said medial panel being constructed of a scent impregnated gel material.

* * * * *